United States Patent
Barla et al.

(10) Patent No.: US 11,370,895 B2
(45) Date of Patent: Jun. 28, 2022

(54) METHODS FOR RECYCLING COTTON AND POLYESTER FIBERS FROM WASTE TEXTILES

(71) Applicant: Circ, LLC, Danville, VA (US)

(72) Inventors: Florin G. Barla, Danville, VA (US); Todd Showalter, Danville, VA (US); Hsun-Cheng Su, Chapel Hill, NC (US); Jeremy Jones, Danville, VA (US); Iulian Bobe, Danville, VA (US)

(73) Assignee: Circ, LLC, Danville, VA (US)

(*) Notice: Subject to any disclaimer, the term of this patent is extended or adjusted under 35 U.S.C. 154(b) by 23 days.

(21) Appl. No.: 17/019,877

(22) Filed: Sep. 14, 2020

(65) Prior Publication Data

US 2020/0407530 A1 Dec. 31, 2020

Related U.S. Application Data

(63) Continuation of application No. 16/695,969, filed on Nov. 26, 2019, now Pat. No. 11,180,629, which is a continuation of application No. 16/246,044, filed on Jan. 11, 2019, now Pat. No. 10,501,599.

(60) Provisional application No. 62/616,543, filed on Jan. 12, 2018.

(51) Int. Cl.

| C08J 11/26 | (2006.01) |
|---|---|
| C08L 1/02 | (2006.01) |
| D06M 13/184 | (2006.01) |
| C07C 63/26 | (2006.01) |
| C08J 11/14 | (2006.01) |
| C07C 51/09 | (2006.01) |
| C08B 16/00 | (2006.01) |

(52) U.S. Cl.
CPC ............... *C08J 11/26* (2013.01); *C07C 51/09* (2013.01); *C07C 63/26* (2013.01); *C08B 16/00* (2013.01); *C08J 11/14* (2013.01); *C08L 1/02* (2013.01); *D06M 13/184* (2013.01); *C08J 2367/02* (2013.01); *C08J 2401/02* (2013.01)

(58) Field of Classification Search
USPC .................................. 521/48, 155, 161, 180
See application file for complete search history.

(56) References Cited

U.S. PATENT DOCUMENTS

| 4,436,586 A | 3/1984 | Elmore |
|---|---|---|
| 5,151,368 A | 9/1992 | Brimhall et al. |
| 5,236,959 A | 8/1993 | Oakley et al. |
| 6,468,390 B1 | 10/2002 | Snekkenes et al. |
| 6,545,061 B1 | 4/2003 | Murdoch et al. |
| 6,772,767 B2 | 8/2004 | Mua et al. |
| 7,544,635 B2 | 6/2009 | Liang et al. |
| 8,268,126 B2 | 9/2012 | Fang |
| 8,460,898 B2 | 6/2013 | Diner |
| 8,546,560 B2 | 10/2013 | Kilambi |
| 8,637,718 B2 | 1/2014 | Gupta |
| 8,679,352 B2 | 3/2014 | Olivier et al. |
| 9,388,529 B2 | 7/2016 | Lindstrom et al. |
| 9,469,693 B2 | 10/2016 | Henriksson et al. |
| 9,611,371 B2 | 4/2017 | Walker |
| 9,751,955 B2 | 9/2017 | Lindstrom et al. |
| 9,902,815 B2 | 2/2018 | Tamminen et al. |
| 10,266,610 B2 | 4/2019 | Varhimo et al. |
| 10,300,464 B2 | 5/2019 | Lin et al. |
| 10,322,395 B2 | 6/2019 | Kumar et al. |
| 10,392,565 B2 | 8/2019 | Xiao et al. |
| 10,603,651 B2 | 3/2020 | Kumar et al. |
| 2004/0154760 A1 | 8/2004 | Dean |
| 2007/0193706 A1 | 8/2007 | Kirov et al. |
| 2008/0097120 A1 | 4/2008 | Jermolovicius et al. |
| 2009/0053777 A1 | 2/2009 | Hennessey et al. |
| 2010/0178677 A1 | 7/2010 | Dunson et al. |
| 2013/0192123 A1 | 8/2013 | Maschmeyer et al. |
| 2013/0276801 A1 | 10/2013 | Byrd, Jr. et al. |
| 2014/0234936 A1 | 8/2014 | Kusuda et al. |
| 2014/0242684 A1 | 8/2014 | Harlick et al. |
| 2014/0275299 A1 | 9/2014 | Bedwell et al. |
| 2014/0331993 A1 | 11/2014 | Kumar et al. |
| 2014/0345341 A1 | 11/2014 | Fiato et al. |
| 2015/0225901 A1 | 8/2015 | Asikainen et al. |

(Continued)

FOREIGN PATENT DOCUMENTS

| CN | 1139719 A | 1/1997 |
|---|---|---|
| CN | 101448581 A | 6/2009 |

(Continued)

OTHER PUBLICATIONS

USPTO, non-Final Office Action in U.S. Appl. No. 16/402,784 dated Jul. 29, 2019.
USPTO, non-Final Office Action in U.S. Appl. No. 16/802,651 dated Oct. 6, 2020.
USPTO, non-Final Office Action in U.S. Appl. No. 15/822,414 dated Aug. 10, 2018.
CNIPA, First Office Action in Chinese Application No. 201680033630.6 dated Sep. 27, 2019.
EPO, Extended European Search Report in European Application No. 16808506.6-1101 dated Mar. 20, 2019.
Toor, Saqib Sohail, et al, Hydrothermal liquefaction of biomass: A review of subcritical water technologies, Energy, 36, 2011, pp. 2328-2342.

(Continued)

*Primary Examiner* — Terressa Boykin
(74) *Attorney, Agent, or Firm* — Dority & Manning, P.A.

(57) ABSTRACT

Systems and methods are provided that involve a subcritical water reaction to recycle the cellulose and polyester components of waste cotton and cotton/polyester blend textiles that would otherwise be discarded or disposed of. Specifically, the disclosed methods provide for treatment of the waste textiles to produce advanced materials including cellulose and terephthalic acid (TPA) with a low environmental impact. The cellulose and TPA that are produced are of a high quality allowing for production of regenerated cellulose and regenerated polyethylene terephthalate (PET) suitable for fiber spinning and textile applications.

14 Claims, 10 Drawing Sheets

(56) References Cited

U.S. PATENT DOCUMENTS

| | | | |
|---|---|---|---|
| 2016/0053058 A1* | 2/2016 | Tabor | C08G 18/44 521/161 |
| 2016/0311997 A1 | 10/2016 | Rangaswamy et al. | |
| 2017/0008826 A1 | 1/2017 | Essaddam | |
| 2017/0218162 A1 | 8/2017 | Walker et al. | |
| 2017/0362775 A1 | 12/2017 | Juvonen et al. | |
| 2018/0002837 A1 | 1/2018 | Yu et al. | |
| 2018/0127515 A1 | 5/2018 | Ropponen et al. | |
| 2018/0347111 A1 | 12/2018 | Lee | |
| 2019/0255506 A1 | 8/2019 | Kumar et al. | |

FOREIGN PATENT DOCUMENTS

| | | |
|---|---|---|
| CN | 102392378 B | 3/2012 |
| CN | 106674588 A | 5/2017 |
| EP | 1383955 B1 | 1/2010 |
| EP | 2171154 A4 | 4/2010 |
| EP | 1454009 B1 | 6/2010 |
| EP | 2425024 B1 | 1/2013 |
| EP | 2247623 B1 | 1/2014 |
| EP | 2452014 B1 | 8/2016 |
| EP | 2817448 B1 | 11/2016 |
| EP | 3172267 A1 | 5/2017 |
| EP | 2678474 B1 | 8/2017 |
| EP | 3307950 A4 | 4/2018 |
| EP | 2632957 B1 | 11/2018 |
| EP | 2895653 B1 | 3/2019 |
| GB | 1562493 A | 3/1980 |
| GB | 2528495 A | 1/2016 |
| GB | 2560726 A | 9/2018 |
| JP | 2009261275 A | 11/2009 |
| JP | 2011032388 A | 2/2011 |
| JP | 2013528715 A | 7/2013 |
| JP | 646399 B2 | 6/2018 |
| JP | 6346399 B2 | 6/2018 |
| WO | 0202871 A1 | 1/2002 |
| WO | 2009008822 A1 | 1/2009 |
| WO | 2010009343 A2 | 1/2010 |
| WO | 2011138633 A1 | 11/2011 |
| WO | 2013124265 A1 | 8/2013 |
| WO | 2014089412 A1 | 6/2014 |
| WO | 2016004482 A1 | 1/2016 |
| WO | 2016012755 A1 | 1/2016 |
| WO | WO2016034727 | 3/2016 |
| WO | 2016193542 A1 | 12/2016 |
| WO | 2017135816 A1 | 8/2017 |
| WO | 2018073177 A1 | 4/2018 |
| WO | 2018104330 A1 | 6/2018 |
| WO | 2018146386 A1 | 8/2018 |
| WO | 2018197756 A1 | 11/2018 |
| WO | 2020084412 A1 | 4/2020 |

OTHER PUBLICATIONS

PCT, International Preliminary Report on Patentability, International application No. PCT/SE2008/050837, dated Aug. 26, 2009.

PCT, International Search Report and Written Opinion, International application No. PCT/US2016/037188 dated Sep. 12, 2016.

JPO, First Office Action in Japanese Application No. 2017-564526 dated Jul. 15, 2020.

PCT, International Preliminary Report on Patentability, International application No. PCT/US2016/037188 dated Dec. 12, 2017.

CNIPA, Second Office Action in Chinese Application No. 2016800336306 dated Jul. 17, 2020.

Australian Government IP Australia, Preliminary search and opinion for your patent application, Australian Application No. 2019206607, dated Sep. 21, 2020.

Palme, Anna, et al., Development of an efficient route for combined recycling of PET and cotton from mixed fabrics, Textiles and Clothing Sustainability, 2017, vol. 3, No. 4, pp. 1-9.

Agrupis, Shirley, et al., Industrial utilization of tobacco stalks II: preparation and characterization of tobacco pulp by steam explosion pulping, The Japan Wood Research Society, 2000, 46, pp. 222-229.

International Search Report and Written Opinion for PCT Application No. PCT/US2019/013270 dated Apr. 29, 2019.

International Search Report and Written Opinion for PCT Application No. PCT/US2017/065334 dated Mar. 30, 2018.

Liguori, Rossana et al. "Bioreactors for lignocellulose conversion into fermentable sugars for product of high added value products", Applied Microbiology and Biotechnology, Nov. 16, 2015 (online), pp. 597-611, vol. 100.

WIPO; International Preliminary Report on Patentability for International Patent Application No. PCT/US2019/013270 dated Jul. 23, 2020, 7 pages.

* cited by examiner

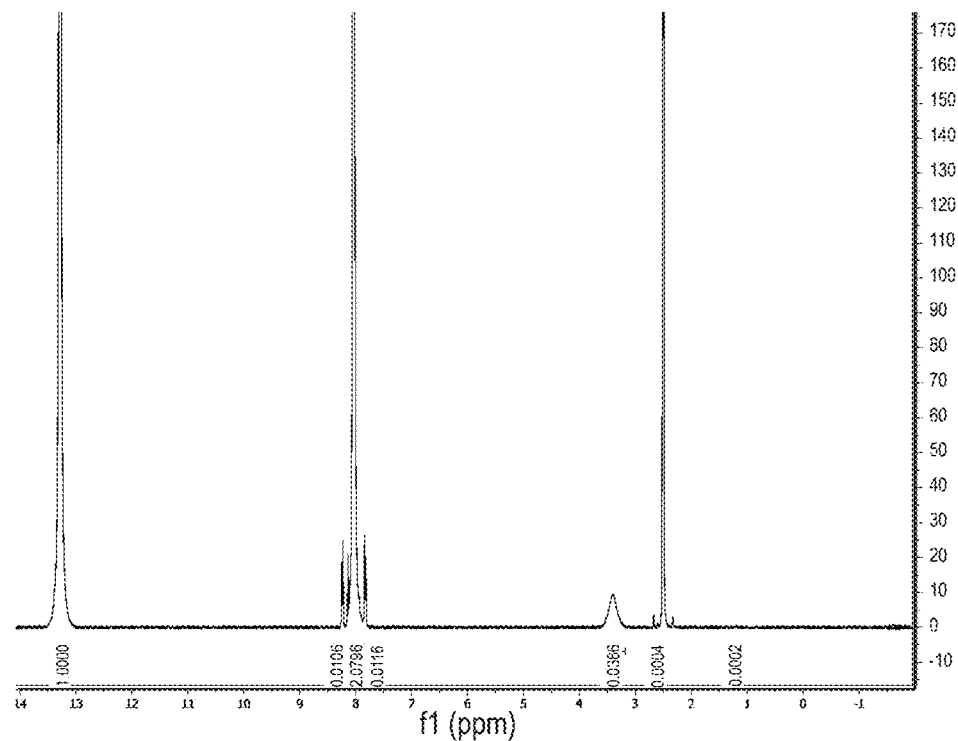
Fig. 9A
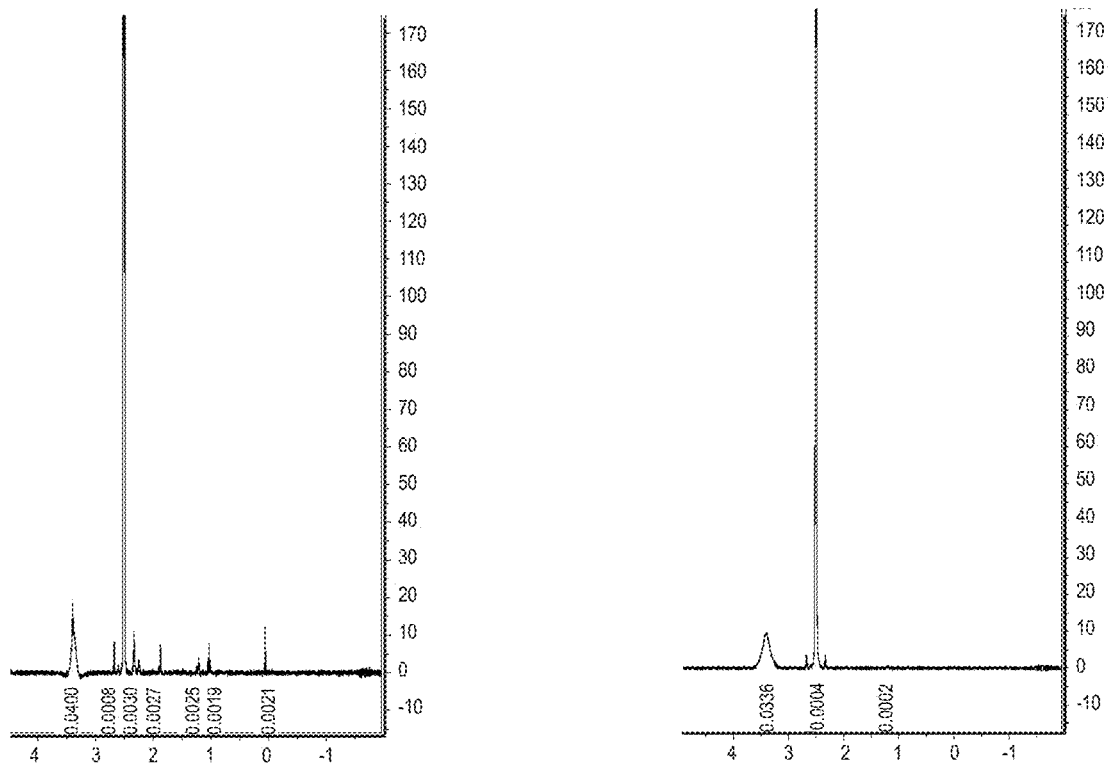
Fig. 9B
Fig. 9C

METHODS FOR RECYCLING COTTON AND POLYESTER FIBERS FROM WASTE TEXTILES

CROSS REFERENCE TO RELATED APPLICATIONS

The present application is a continuation of U.S. patent application Ser. No. 16/695,969 filed on Nov. 26, 2019, which is a continuation of U.S. patent application Ser. No. 16/246,044 filed on Jan. 11, 2019, now U.S. Pat. No. 10,501,599 issued on Dec. 10, 2019, which claims the benefit under 35 U.S.C. § 119(e) of U.S. Provisional Patent Application No. 62/616,543 filed on Jan. 12, 2018, the entire contents of all of which are incorporated herein by reference.

TECHNICAL FIELD

The presently disclosed subject matter relates to a system and method for recycling the components of cotton and polyester from textiles. The presently disclosed subject matter further relates to a method of producing high quality components of cotton and polyesters enabling the production of advanced materials using an environmentally-friendly method.

BACKGROUND

In the textile industry, finished apparel and related goods have a limited lifespan. When they have ended their useful life, they typically end up in a landfill or waste incineration facility. It is estimated that more than 15 million tons of used textile waste is generated each year in the United States. Regenerated fibers have become increasingly popular as a sustainable alternative to natural virgin fibers, such as cotton. In general, textiles for recycling are generated from two primary sources, including: (1) pre-consumer sources, such as scrap created as a by-product from yarn and fabric manufacture; (2) post-consumer sources, such as garments, vehicle upholstery, household items, and others. Current textile recycling is fundamentally divided into two groups for processing. For natural textiles (such as 100% cotton), materials are shredded or pulled into fibers and then processed into yarn for re-spinning and prepared for subsequent use in weaving and/or knitting. For polyester-based textiles, garments are shredded and then granulated and processed into polyester chips. The chips are subsequently melted and used to create new fibers for use in the polyester fabrics. However, conventional methods of recycling and/or regenerating textiles are associated with significant drawbacks, such as the use of expensive and harsh hydrolyzing agents, complex recycling methods, waste water discharge, pollution, energy use that renders the process cumbersome, and significant expenditures of time. It would therefore be beneficial to overcome the shortcomings of current technology by providing a simple and cost-effective method of regenerating premium recycled fibers that significantly reduces chemical usage and waste water production.

SUMMARY

In some embodiments, the presently disclosed subject matter is directed to a method of producing one or both of cellulose and terephthalic acid (TPA) from waste textile material comprising essentially 100% cotton or cotton/polyester blend material. Particularly, the method comprises treating the waste textile material in a subcritical water reactor at a temperature of about 105° C. to 190° C., a pressure of about 40 to 300 psi, or both for about 0 to 90 minutes, wherein one or both of a cellulose that comprises a degree of polymerization ranging from about 150-2500 and a dissolved TPA and ethylene glycol (EG) are produced. A product comprising cellulose with a degree of polymerization of about 150-2500 and/or a product comprising a recycled terephthalic acid (TPA) is thereby produced. In some embodiments, the cellulose is further recovered, including by a dissolution process to form regenerated cellulose.

In some embodiments, the waste textile material comprises cotton/polyester blend material and the treating in the subcritical water reactor comprises a pH ranging from about 10-14. The method can further comprise recovering the TPA. The method can further comprise recovering the cellulose. The method can further comprise subjecting the recovered cellulose to a disintegration process.

In some embodiments, the waste textile material comprises cotton/polyester blend material and the treating in the subcritical water reactor comprises a first treating at a pH ranging from about 10-14, wherein the TPA is produced, and a second treating of the cellulose that is produced in the first treating at a pH ranging from about 2-4, wherein the cellulose that is produced in the second treating comprises a degree of polymerization ranging from about 150-2000. In some embodiments, the cellulose with a degree of polymerization of about 150-2500 is of a purity ranging from about 94%-98%. The method can further comprise recovering the cellulose produced after the second treating, including by subjecting the cellulose to one or more steps of wash, disintegration, sour wash, activation process, dissolution dope, or wet spinning.

The method allows for reducing the size of cellulose fibers in the waste textile material, loosening the cellulose fibers from the waste textile material, or both.

In some embodiments, the method further comprises sorting the waste textile material before or after treatment in the subcritical water reactor. In some embodiments, the sorting is based on color, composition, weight percent cellulose, non-cellulose components, or combinations thereof.

The method allows for dissolving cellulose fibers present within the waste textile material.

In some embodiments, the method further comprises a pretreatment step reducing the size of the waste textile material. The pretreatment step can be by mechanical cutting. In some embodiments, the reducing generates a particle size of about 60 mm or less.

In some embodiments, the method further comprises removing color from the waste textile material before, during, or after treating with the subcritical water reactor. In some embodiments, the color removal comprises treatment with one or more of hydrogen peroxide, sodium peroxide, sodium hypochlorite, calcium hypochlorite, dimethyl sulfoxide, lithium hypochlorite, sodium perborate, ozone, oxygen, activated carbon, biochar, sodium carbonate, peracetic acid, potassium permanganate, persulfate, sodium chloride, calcium oxychloride, chloramine, chlorine dioxide, sulfur dioxide, sodium hydrosulfite, or TAED (tetra-acetyl-ethylene-di-amine).

In some embodiments, the subcritical water reactor treatment comprises one or more of methanol, ethanol, isopropanol, tetra-n-butylphosphonium bromide (TBPB), or benzyltributylammonium chloride (BTBAC), or co-polymers thereof.

In some embodiments, the ratio of waste textile material to water within the subcritical water reactor is about 1:5-1:95.

In some embodiments, the method further comprises subjecting the waste textile material to acid treatment in the subcritical water reactor. The cellulose in the waste textile material can then be subjected to a mechanical disintegration process. This method can allow for recovering the cellulose in the waste textile material to produce regenerated cellulose.

In some embodiments, the method further comprises adjusting the pH of water within the subcritical water reactor before subcritical water treatment. In some embodiments, the pH is adjusted to about 2-4. In some embodiments, the pH is adjusted to about 10-14. In some embodiments, the pH is adjusted using 0.01-5% (v/v) organic acid, 0.5-20% (w/v) sodium hydroxide, or 0.5-20% (w/v) potassium hydroxide.

In some embodiments, wherein the waste textile material comprises a cotton/polyester blend, the subcritical water reactor functions to decompose the polyester and adjust the degree of polymerization of the cellulose macromolecules.

In some embodiments, the subcritical water reactor enables the dissolution of polyester to terephthalic acid (TPA) and ethylene glycol (EG).

In some embodiments, a method is provided for producing terephthalic acid (TPA) from a polyester waste textile material, the method comprising: treating the polyester waste textile material in a subcritical water reactor at a temperature of about 105° C. to 190° C., a pressure of about 40 to 300 psi, or both for about 0 to 90 minutes, wherein a dissolved TPA and ethylene glycol (EG) is produced. The pH can range from about 10-14. The method can further comprise precipitating and recrystallizing the TPA.

In some embodiments, the presently disclosed subject matter is directed to a regenerated cellulose material produced using the disclosed method. In some embodiments, the presently disclosed subject matter is directed to a regenerated polyester material produced using the disclosed method. In some embodiments, the products of regenerated cellulose material include rayon, viscose rayon, lyocell, or cellulose acetate. The regenerated cellulose and TPA have properties making them suitable for fiber spinning and textile applications. For example, in one embodiment, the regenerated cellulose monofilaments of the present disclosure have a tenacity ranging from 1.3 g/den to 1.8 g/den and a strain at break of about 10% to 12%.

BRIEF DESCRIPTION OF THE DRAWINGS

The previous summary and the following detailed descriptions are to be read in view of the drawings, which illustrate some (but not all) embodiments of the presently disclosed subject matter.

FIG. 9A is an NMR analysis of crystallized TPA from a water recrystallization step produced in accordance with some embodiments of the presently disclosed subject matter.

FIG. 9B is an NMR analysis of precipitated TPA powder from polycotton fabrics produced in accordance with some embodiments of the presently disclosed subject matter.

FIG. 9C is an NMR analysis of crystallized TPA from a water recrystallization step produced in accordance with some embodiments of the presently disclosed subject matter.

DETAILED DESCRIPTION

Figure 1:
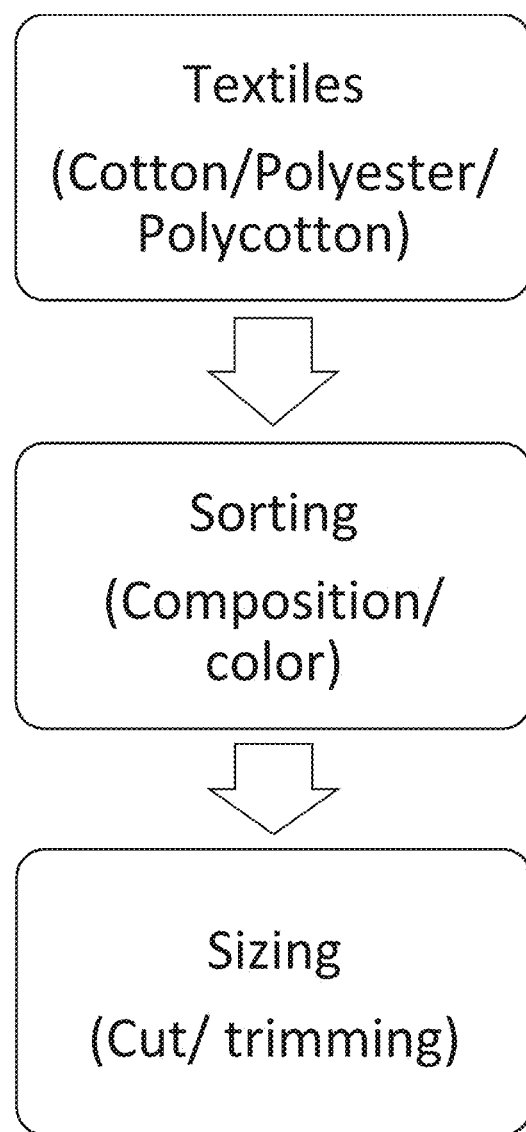
FIG. 1 is a schematic of one embodiment of a sorting/sizing method that can be used in accordance with the presently disclosed subject matter.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a reactor" can include a plurality of such reactors, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed methods.

The presently disclosed subject matter is directed to a system and method of processing cellulose-comprising materials, polyester-comprising materials, and/or polycotton (polyester-cotton)-comprising materials, such as pre-consumer or post-consumer textiles, fabric scraps, and other materials that would otherwise be discarded or disposed of. Specifically, the disclosed system and method provides for treatment of textiles that include cellulose, polyester, and/or cellulose blended with polyester. Regenerated cellulose and PET filaments are produced from the waste textile materials according to the methods of the present disclosure. The terms "regenerated" and "recycled" are herein used interchangeably for the purposes of the specification and claims. Implementation of the disclosed system and method can produce regenerated fibers and textile products with improved properties using processes with low environmental impacts. For example, in one embodiment, the regenerated cellulose monofilaments of the present disclosure have a tenacity ranging from 1.3 g/den to 1.8 g/den and a strain at break of about 10% to 12%.

In the presently disclosed system and method, any material that comprises cellulose, polyester, and/or polycotton can be used as the starting material. For example, in some embodiments, the starting material can be a waste cotton and/or waste polycotton (cotton/polyester blend) material found in post-consumer waste textiles and other cellulose-containing fabrics (towels, bedding, upholstery, etc.). For the purposes of the specification and claims, the terms "polycotton" and "cotton/polyester blend" are herein used interchangeably. Cotton fiber is the only natural pure cellulose, with a cellulose content of up to about 95-97 weight percent. The term "cellulose" as used herein refers to a polysaccharide having the formula $(C_6H_{10}O_5)_n$ configured as a linear chain of β(1→4) linked D-glucose units (cellobiose), as illustrated in Structure (I), below:

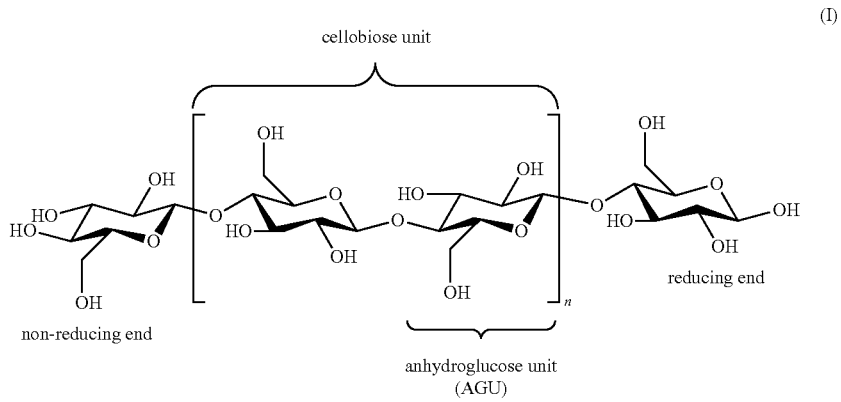

(I)

cellobiose unit non-reducing end anhydroglucose unit (AGU)

reducing end

The individual glucose monomers in the cellulose polymer are often referred to as anhydroglucose units (or "AGU"). The number of AGU units defines as the "Degree of Polymerization" (DP) of the cellulose. In the presently disclosed system and method, viscosity measurements can be used to assess changes in the DP of cellulose in cellulosic pulp after subcritical water treatment. For the purposes of the specification and claims, the terms "cellulosic pulp", "pulp", "cotton pulp", and "cotton sheet" are herein used interchangeably, and refer to the cellulose that is produced from the waste textile fabric by the subcritical water treatment of the present disclosure. The cellulose viscosity (unit in mPa·s) is determined according to TAPPI T230 om-94 (1994) (incorporated herein by reference) in cupriethylenediamine (CED) solution. The intrinsic viscosity [η] (unit in ml/g) can be calculated from Equation 1 below (Mazumder B. B. et al. 2000, *Journal of Wood Science* 46(5), 364-370):

$$[\eta]=954\times\lg(\text{viscosity})-325 \qquad \text{Equation 1:}$$

The average DP can be calculated from the intrinsic viscosity using Equations 2 (Sihtola et al. 1963; *Paper Ja Puu* 45, 225-232) and 3, below:

$$DP^{0.905}=0.75\times[\eta] \qquad \text{Equation 2:}$$

$$DP=k\times[\eta]; K=1.9 \qquad \text{Equation 3:}$$

In the presently disclosed system and method, the subcritical water-treated textile cellulosic pulp can have a viscosity range of about 3 mPa·s to about 55 mPa·s, which refers to a DP of about 150-2500, such as about 200-2000, 300-1700, 400-1500, 500-1200, 600-1000, or 700-800. Thus, the treated cellulosic pulp can have a DP of at least about (or no more than about) 150, 200, 300, 400, 500, 600, 700, 800, 900, 1000, 1100, 1200, 1300, 1400, 1500, 1600, 1700, 1800, 1900, 2000, 2100, 2200, 2300, 2400, or 2500.

Polyesters are a group of polymers commonly used in textile applications. The polymer is a very large molecule build up from smaller molecules. The most common type of polyester used in textiles is polyethylene terephthalate (PET) (Structure II, below), which can combine with cotton fiber to form polycotton.

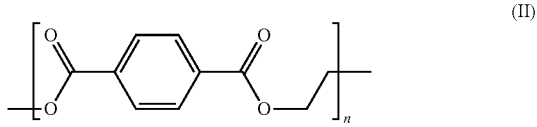

(II)

The term "textile" is broadly used herein, and includes fibers, filaments, yarns, woven and non-woven fabrics, knits, and finished products (such as garments).

As set forth in FIG. 1, the disclosed system comprises a sorting component where the waste textiles are sorted according to one or more desired parameters. For example, in some embodiments, the waste textiles can be sorted according to composition, such as to separate 100% cotton materials from cotton/polyester blends and the like. In some embodiments, the textiles can be sorted according to cellulose content (e.g., >90%, >80%, >70%, >60%, >50% or <50% cellulose). In some embodiments, the textiles can be sorted to separate out non-cellulosic material, such as zippers, tags, buttons, and the like. In some embodiments, the textiles can be sorted according to color. The sorting step can be accomplished using any known mechanical sorting device or can be done by hand.

In some embodiments, the methods of the present disclosure comprise a mechanical cutting device that is configured to reduce the textile size and/or to provide a more uniform textile size prior to further treatment. Typically, textile materials that include cotton, fabric, yarn, and fibers have a fiber length of greater than 5 mm to 100 mm. In some embodiments, the cutting device reduces the fiber length to about 60 mm or less. The cutting device can include any device capable of trimming textile size, such as (but not limited to) one or more blades, needles, shredders, pullers, grinders, cutters, rippers, and the like. In some embodiments, the waste textiles are cut to a size of about 5-60 mm in length and/or width. However, the presently disclosed subject matter is not limited, and the waste materials can be cut into any desired size. Advantageously, reducing the size of the cellulosic textile material increases the surface area for further treatment (e.g., subcritical water treatment).

Figure 2:
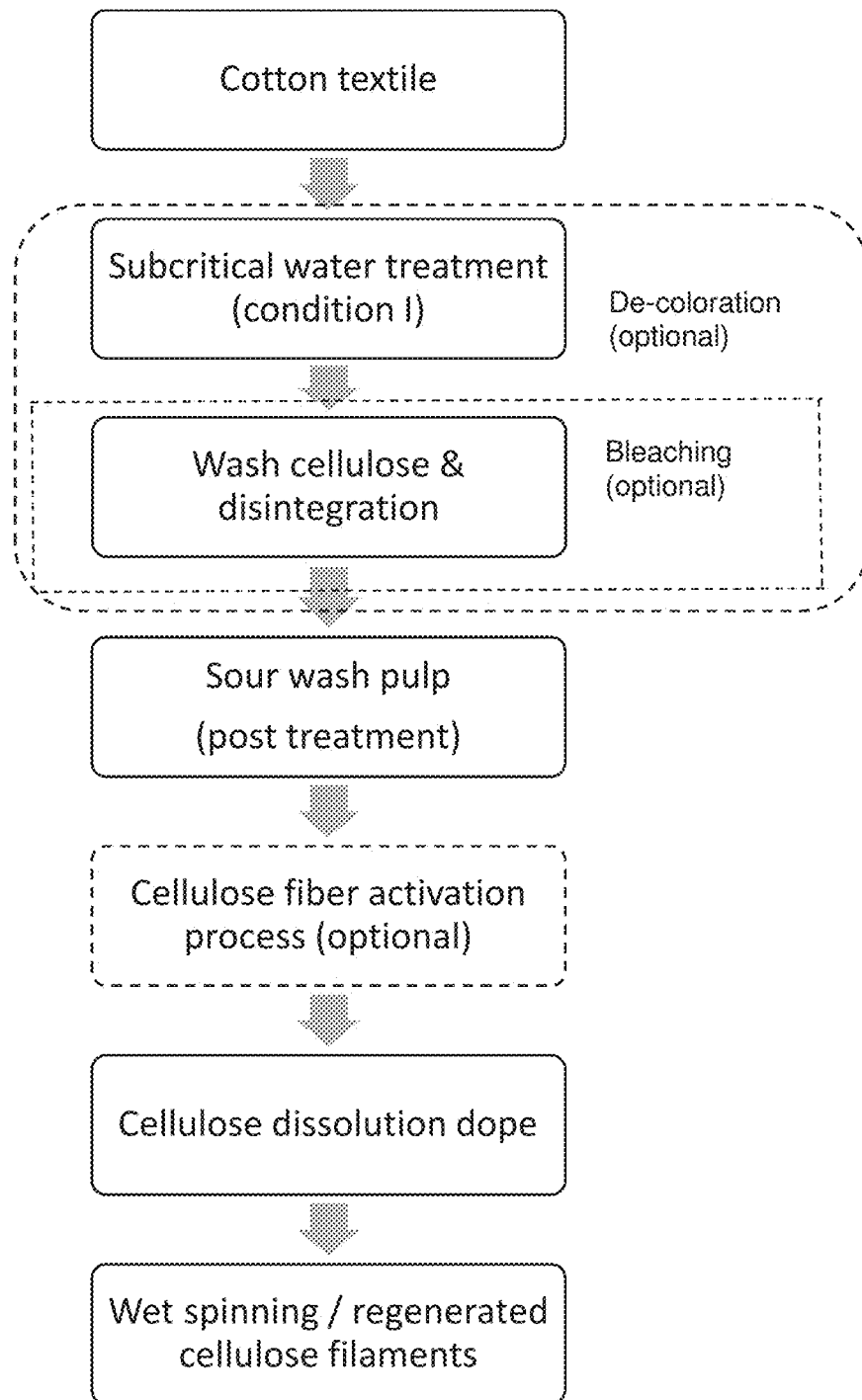
FIG. 2 is a schematic of one embodiment of a method for producing regenerated fibers from cotton textiles in accordance with some embodiments of the presently disclosed subject matter. The dashed lines indicate optional processing steps of de-coloration, bleaching, and cellulose fiber activation.
Figure 3:
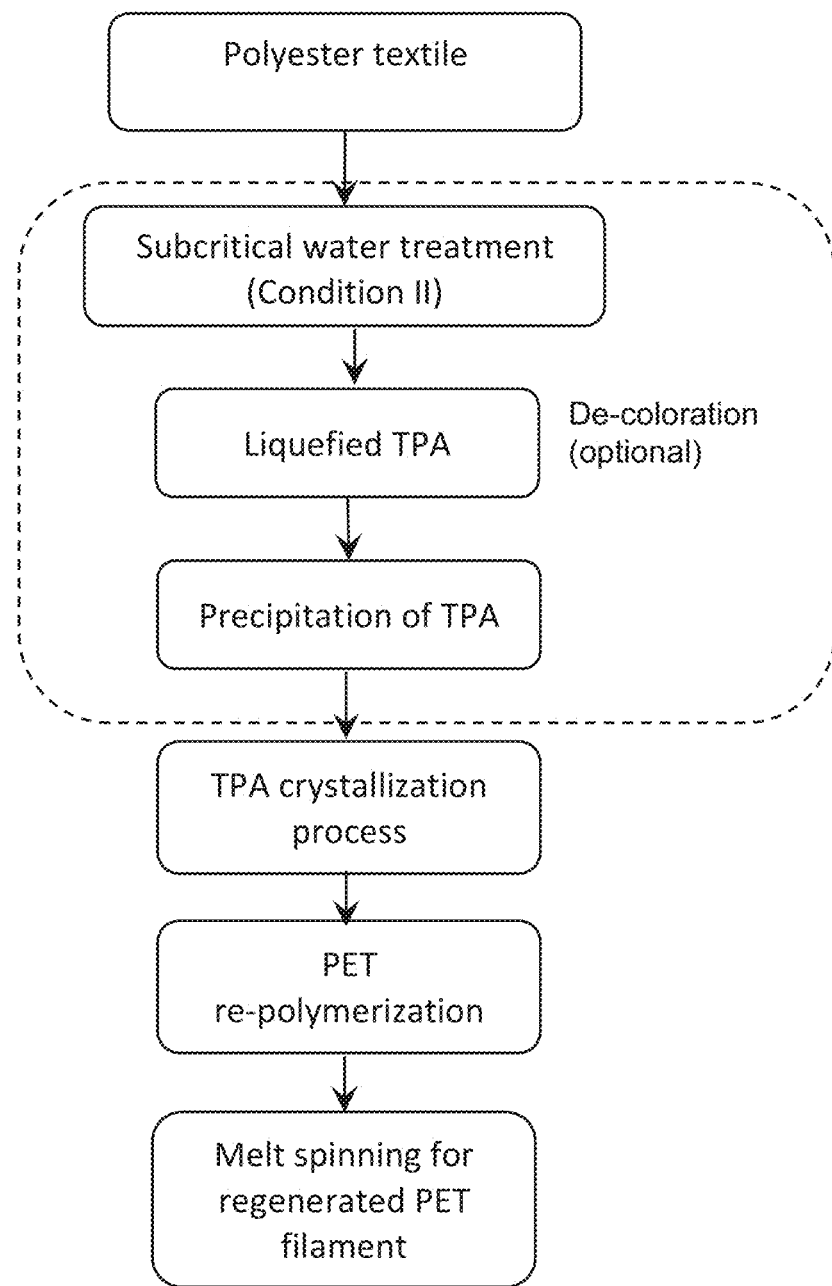
FIG. 3 is a schematic of one embodiment of a method for producing regenerated fibers from polyester textiles in accordance with some embodiments of the presently disclosed subject matter. The dashed line indicates the optional processing step of de-coloration.
Figure 4:
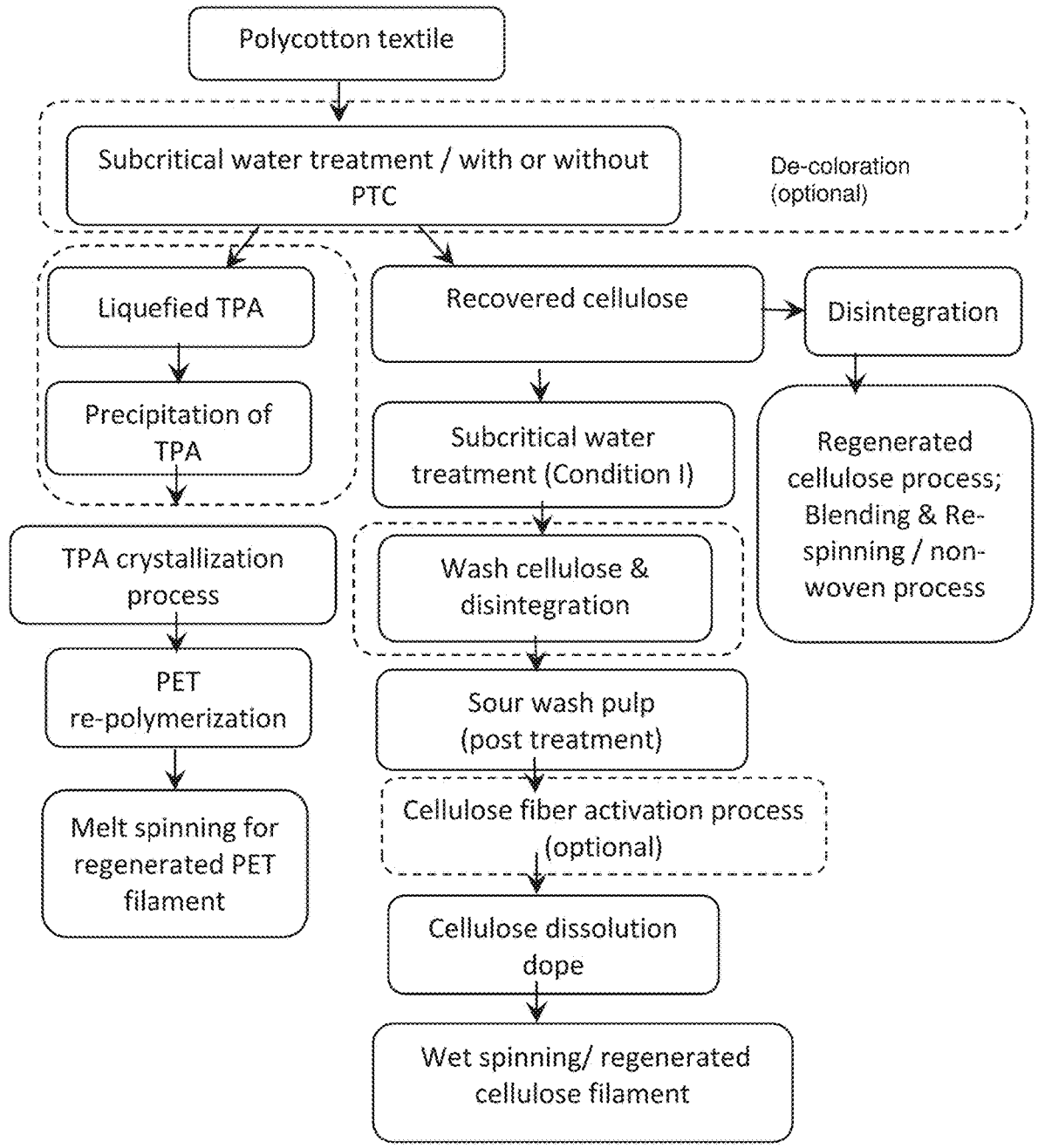
FIG. 4 is a schematic of one embodiment of a method for producing regenerated fibers from polycotton textiles in accordance with some embodiments of the presently disclosed subject matter. The dashed lines indicate the optional processing steps of de-coloration, bleaching, and cellulose fiber activation.

In some embodiments, the sorting process can be conducted by manual platform or any known current waste textile automation recycling machine to separate the materials into three streams, as shown in FIGS. 2, 3, and 4. Particularly, stream 1 can comprise essentially 100% cotton, stream 2 can comprise essentially 100% polyester, and stream 3 can comprise polycotton (cotton and polyester in any ratio). In some embodiments, the sorting process can initially scan using an optical sensor to separate the waste textiles by color. The materials can then be scattered thoroughly by a uniform distributing machine. Non-cellulosic materials (such as zippers, tags, buttons, and the like) can then be removed. The sorting and sizing steps can optionally be repeated to enhance the efficiency of the disclosed fiber regeneration process.

The methods of the present disclosure comprise a subcritical water reactor. Particularly, the waste textiles are introduced to the reactor for treatment with subcritical water to weaken the linkage between the fibers in the textiles. The subcritical water reactor further functions to decompose the polyester and adjust the degree of polymerization of the cellulose macromolecules. In addition, the subcritical water reactor enables the dissolution of polyester to terephthalic acid (TPA) and ethylene glycol.

The term "reactor" as used herein refers to a device that can be used for any number of chemical processes involving a starting material. In some embodiments, the reactor comprises a hydrothermal reactor. The term "hydrothermal" as used herein refers to an aqueous system under pressure and increased temperature, typically near or below the critical point of water (374° C., 22.1 MPa). Thus, the reactor can provide hydrothermal conditions, such as (but not limited to) a batch reactor, semi-continuous, or continuous reactor. In some embodiments, a batch reactor is preferred. The term "subcritical water" as used herein refers to liquid water at temperatures between the atmospheric boiling point (100° C.) and the critical temperature (374° C.) that present unique features with respect to its properties, such as density, dielectric constant, ion concentration, diffusivity, and solubility. In the subcritical region, the ionization constant (Kw) of water increases with temperature and is about three orders of magnitude higher than that of ambient water, and the dielectric constant of water drops from 80 to 20.

Advantageously, subcritical water is a non-toxic, environmentally benign, inexpensive, and green solvent that can be used as an alternative to harsh chemicals traditionally used in the fabric recycling industry. In the disclosed method and the system, the use of subcritical water hydrothermal treatment allows higher diffusion, activity, and ionization of water. In some embodiments, the partial hydrolysis of cellulose and the breakdown of the cross-link between the cotton cellulose and polyester in the textile can be achieved.

In some embodiments, adjustable hydrothermal reaction conditions can be applied to produce cellulose in a broad desired DP range (DP: 150-2500) that can be used to manufacture a wide variety of regenerated cellulose products, such as rayon, viscose rayon, lyocell, lyocell-like, or cellulose acetate. In some embodiments, the subcritical water reactor can mix with one or more co-solvents (e.g., methanol, ethanol, isopropanol) such that a temperature of about 105° C. to 190° C. (e.g., about 105-190, 110-180, 120-175, 130-160, 140-150, 140-170, 150-160, 160-190, 170-180, 165-190, or 175-185° C.) and/or a pressure of about 40 to 300 psi (e.g., about 40-300, 60-280, 80-250, 80-120, 110-140, 120-150, or 100-250 psi) can be achieved for residence time about 0 to 90 minutes (e.g., about 0-90, 10-80, 20-70, 30-60, 40-70, or 40-50 minutes). In some embodiments, the co-solvents can be present in an amount of from about 0-100 weight percent, such as about 1-90, 5-80, 10-70, 20-60, or 30-50 weight percent.

In some embodiments, the disclosed method can include a phase transfer catalyst (PTC) to improve the process efficiency and to reduce energy consumption. The term "phase transfer catalyst" refers to any agent capable of facilitating a reactor by virtue of the ability to dissolve as ion pairs in both aqueous and organic solvents. Any desired PTC can be used, such as (but not limited to) any commercially available ammonium or phosphonium-based PTC, such as tetra-n-butylphosphonium bromide (TBPB), benzyltributylammonium chloride (BTBAC), or co-polymers etc.

The waste textiles can be transferred to the reactor and processed for a desired amount of time. In some embodiments, the textiles can be treated in the reactor at a temperature of about 105° C. to 190° C., at a pressure of about 40 to 300 psi, or both. In some embodiments, the ratio of textile material to water is about 1:5-1:95 (e.g., 1:5, 1:10, 1:11, 1:12, 1:13, 1:14, 1:15, 1:20, 1:21, 1:22, 1:23, 1:24, 1:25, 1:30, 1:31, 1:32, 1:33, 1:34, 1:35, 1:40, 1:45, 1:50, 1:55, 1:60, 1:65, 1:70, 1:75, 1:80, 1:81, 1:82, 1:83, 1:84, 1:85, 1:86, 1:87, 1:88, 1:89, 1:90, 1:91, 1:92, 1:93, 1:94, 1:95). In some embodiments, the reaction time can be about 0-90 minutes, such as at least about (or no more than about) 0, 5, 10, 15, 20, 25, 30, 35, 40, 45, 50, 55, 60, 65, 70, 75, 80, 85, or 90 minutes.

In the reactor, the linkage between the fibers in the textiles is weakened as a result of the temperature and/or pressure. Particularly, the high temperature and/or pressure of the subcritical water promotes molecular separation of the cellulose polymers and deconstructs intermolecular hydrogen bonds and other non-covalent bonds within the waste textiles. As a result, the cellulose-containing textiles are converted to their constituent cellulose polymers. In some embodiments, the number of intermolecular hydrogen bonds in the cellulosic material is reduced by at least 20%, 30%, 40%, 50%, 60%, 70%, 80%, or 90% after the subcritical water treatment. Thus, treatment with subcritical water provides an environmentally-friendly way to break down the cellulose in the waste textile materials.

In some embodiments, the pH of the starting material (e.g., water and textile mixture) in the reactor can be adjusted to enhance subcritical water reaction efficiency. For example, 0.01%-2% acetic acid can be used with cotton textile to adjust the pH to about 4. In some embodiments, the pH can be adjusted to a range of about 2 to 4 for cotton textile. For cotton/polyester textile blends, 0.01%-5% acetic acid can be used to generate a pH of 2-4. In embodiments where the textile comprises cotton/polyester blends and/or polyester, 0.5-20% sodium hydroxide (NaOH) or potassium hydroxide (KOH) can be used to achieve a pH of about 10-14. In some embodiments, polyester (PET) textile can be degraded via hydrolysis using 0.5-20% NaOH, and can further be dissolved through a subcritical water treatment. However, it should be appreciated that the acid/base is not limited, and any suitable acid or base can be used to adjust the pH to a desired level. In some embodiments, the KOH, NaOH, acetic acid, and/or other organic acids function as a reagent to increase the rate of the reaction.

As illustrated in FIG. 2 and described in EXAMPLES 1 through 4, in embodiments wherein the starting textile material is essentially 100% cotton textile (e.g., shredded textile material), the disclosed method includes depositing the material in a subcritical water reactor (e.g., Condition I, an appropriate pH, e.g. pH 2-pH 6 or pH 2-4 and temperature adjustment, 105° C.-190° C.).

In one embodiment, the cellulose resulting from the subcritical water reaction is washed and subjected to a disintegration process to loosen the cellulose fibers as described in EXAMPLES 1 through 4. In this manner the cellulose can be further processed for dissolution. In some embodiments, after this treatment, the disintegrated fibers are subjected to a sour wash pulp process, which entails a treatment with dilute aqueous sulfur dioxide solution using industry standard conditions. A cellulose fiber activation process may be initiated when utilizing certain dissolution systems. This involves producing a ground cellulose pulp sample in aqueous NaOH solution (e.g., 12-15% w/v), 1:20 (cellulose sample:aqueous solution), stirring at room temperature for 3-4 hours, washing to neutral pH, drying, subjecting to an acid treatment (e.g., with 1M sulfuric acid for 45-60 minutes), washing to neutral pH, and air drying. Cellulose dissolute dope can then be prepared by incorporating a dissolving component. The cellulose can be dissolved with molten organic salts (e.g., ionic liquids), such as N-alkylpyridium salts and similar agents, amine oxides (such as N-methylmorpholine-N-oxides and similar agents), and/or polar and aprotic liquids (such as N, N-dimethylacetamide/LiCl and similar agents) to provide a dissolved cellulose suitable for regenerated fiber production utilizing industrial standard techniques.

As illustrated in FIG. 3 and described in EXAMPLE 5, in embodiments wherein the starting textile material is essentially 100% polyester textile (e.g., cut textile material), the disclosed method includes depositing the material in a subcritical water reactor (e.g., Condition 2, at an appropriate pH (e.g. pH 10-14) and with a temperature adjustment (105° C.-190° C.). After treatment, the processed solution can be removed and terephthalic acid (TPA) formed by precipitation by adjusting the pH (e.g., to pH 2-6). The TPA can then be carried forward to crystallization. This entails heating an aqueous solution with precipitated TPA to a temperature of about 250° C. to 300° C., a ratio of solid:water of about 1:4 to 1:10, with a residence time of about 0 to 10 minutes (e.g., 1, 2, 3, 4, 5, 6, 7, 8, 9, or 10 minutes). The crystalized TPA can then be subjected to a PET polymerization process to produce regenerated PET. This process can involve treating the crystallized TPA with ethylene glycol in an industry standard batch autoclave at temperatures between 235° C.-290° C. with appropriate catalyst (e.g. antimony or titanium catalyst packages). Additionally, ethylene glycol can be recovered from the processed solution using industry standard techniques (e.g. vacuum distillation).

As illustrated in FIG. 4 and described in EXAMPLES 6 through 9, in embodiments where the starting textile material includes cotton/polyester blends, the subcritical water treatment (e.g., Condition II, an appropriate pH (e.g. pH 10-pH14) and temperature adjustment (e.g., 105° C.-190° C.)) can be effective to separate the cotton from the dissolved polyester monomers; TPA and ethylene glycol. Particularly, the subcritical water treatment produces liquefied polyester monomers, and cellulose. After treatment, the processed solution is removed and TPA is formed by precipitation using an appropriate pH adjustment (e.g., pH 2-6). The TPA can then be carried forward to crystallization, which entails heating an aqueous solution with precipitated TPA to a temperature of about 250° C. to 300° C., a ratio of solid:water of about 1:4 to 1:10, with a residence time of about 0 to about 10 minutes (e.g., 1, 2, 3, 4, 5, 6, 7, 8, 9, or 10 minutes). The crystalized TPA can then be subjected to a PET polymerization process to produce regenerated PET. This process can involve treating the crystallized TPA with ethylene glycol in an industry standard batch autoclave at temperatures between 235° C.-290° C. with an appropriate catalyst (e.g. antimony or titanium catalyst packages). Additionally, ethylene glycol can be recovered from the processed solution using industry standard techniques (e.g. vacuum distillation).

The waste textiles can be partially or fully treated to remove coloring (e.g., pigments, dyes, etc.) and/or to improve brightness throughout the subcritical water hydrothermal process by adding about 0.5-20% NaOH. Any conventional de-coloration/dye removal element can be used. For example, in some embodiments, the de-coloration/dye removal element can be selected from one or more of hydrogen peroxide, sodium peroxide, sodium hypochlorite, calcium hypochlorite, dimethyl sulfoxide, lithium hypochlorite, sodium perborate, activated carbon powder, biochar, ozone, oxygen, sodium carbonate, peracetic acid, potassium permanganate, persulfate, sodium chloride, calcium oxychloride, chloramine, sulfur dioxide, sodium hydrosulfite, or TAED (tetra-acetyl-ethylene-di-amine).

Further, the disclosed system can comprise a disintegration component. Specifically, after subcritical water reaction, the cellulose can be recovered and subjected to a disintegration component where the cellulose fibers are loosened from the textile pulp as shown in FIG. 4. Any conventional disintegration method can be used, such as (but not limited to) ultrasound, homogenization, and/or grinding.

Further, the disclosed system can comprise a dissolving component wherein the cellulose is dissolved by molten organic salts (e.g., ionic liquids), such as N-alkylpyridium salts and similar agents, amine oxides (such as N-methyl-morpholine-N-oxides and similar agents), and/or polar and aprotic liquids (such as N, N-dimethylacetamide/LiCl and similar agents). In some embodiments, the dissolving component can include one or more additives at a concentration of about 0.1% to 15 weight % (e.g., 0.1, 0.5, 1, 2, 3, 4, 5, 6, 7, 8, 9, 10, 11, 12, 13, 14, or 15 weight %). The additives can promote the production of regenerated cellulose filaments with enhanced mechanical properties (such as higher tenacity and elongation additives). Suitable additives can include (but are not limited to) glyceric acid, gluconic acid, glucuronic acid, galacturonic acid, iduronic acid, mucic acid, and/or glucaric acid. In some embodiments, the dissolving component can comprise powdered titanium dioxide (e.g., 0.1-10 weight %) to produce semi-dull or dull filaments.

After the disintegration of the cellulose fibers, the isolated cellulose molecules can be used to form regenerated cellulose fibers and textile materials. In some embodiments, "regenerated cellulose" refers to cellulose that has been prepared by regeneration (i.e., returned to solid form) from a solution that includes dissolved cellulose fibers. In some embodiments, the isolated cellulose molecules can be dissolved by molten organic salts (e.g., ionic liquids), such as N-alkylpyridium salts and similar agents, amine oxides (such as N-methylmorpholine-N-oxides and similar agents), and/or polar and aprotic liquids (such as N, N-dimethylacetamide/LiCl and similar agents), and spun in a coagulation bath to produce regenerated cellulosic fibers, such as rayon, viscose rayon, lyocell, lyocell-like, or cellulose acetate. The newly formed fibers can be stretched and/or blown to a desired configuration, washed, dried, and cut to a desired length. The regenerated cellulosic fibers can be twisted into thread, dyed, bleached, woven into textiles, and ultimately can be cut and sewn into garments. Thus, the treated fabric can be used to manufacture a garment such as (but not limited to) shirts, pants, hats, coats, jackets, shoes, socks, uniforms, athletic clothing, and swimwear. It is also possible and contemplated that the treated fabric can be used to construct non-apparel items, such as blankets, sheets, sleeping bags, backpacks, tents, insulation materials, and the like.

Thus, in use, the disclosed system can be used to recycle one or both of cellulose and terephthalic acid (TPA) and ethylene glycol (EG) from any starting textile material comprising cellulose, polyester, and/or polycotton. The recycled cellulose can be used to produce regenerated cellulose and the recycled terephthalic acid (TPA) and ethylene glycol (EG) can be used to produce regenerated PET. Particularly, the waste textiles can be provided and sorted based on desired parameters (e.g., percentage cellulose, composition, color, and the like). The sorted textiles can be exposed to a cutting device, blending device, or both to ensure that the textile material is of a suitable size and uniform size for treatment. The cut and/or blended textile material can be optionally bleached to remove or decrease the amount of dyes, finishes, and/or contaminants. The textile material is introduced to a reactor where a subcritical water reaction is performed for a temperature, pressure, and time sufficient to dissolve PET and weaken the linkage between the cellulose fibers (e.g., Condition II, an appropriate pH, e.g., pH 10-pH 14, and temperature adjustment, e.g., 105° C.-190° C.). Dissolved TPA then can be precipitated through pH adjustment, filtered under vacuum, and washed to neutral condition. The washed TPA can be dried and carried forward to crystallization. Crystalized TPA can be subjected to a PET repolymerization process to produce regenerated PET. The cotton cellulose material can be recovered. In some embodiments, the recovered cellulose materials can be disintegrated and can be used to produce regenerated cellulose fibers. In some embodiments, the recovered cellulose material can be disintegrated as staple fiber to blend with either virgin cotton fibers or other fibers as recycled cotton blend yarn. In some embodiments, the recovered cellulose material can be washed and cut into in smaller pieces. The pieces can have an average size ranging from about 4-6 mm. The pieces can be subjected to a second subcritical water treatment (e.g., Condition I, an appropriate pH, e.g., pH 2-pH 4, and temperature adjustment, e.g., 105° C.-190° C.) such as described in EXAMPLES 6 through 8. Subcritical water treated waste textiles can be exposed to a disintegration component where the cellulose fibers are loosened from the pulp material such as described in Example 10. The recovered cellulose is then exposed to a dissolving component to promote dissolving of the cellulose. After the dissolving of the cellulose fibers, the isolated cellulose molecules can be used to form regenerated cellulose fibers and textile materials.

Figure 5:
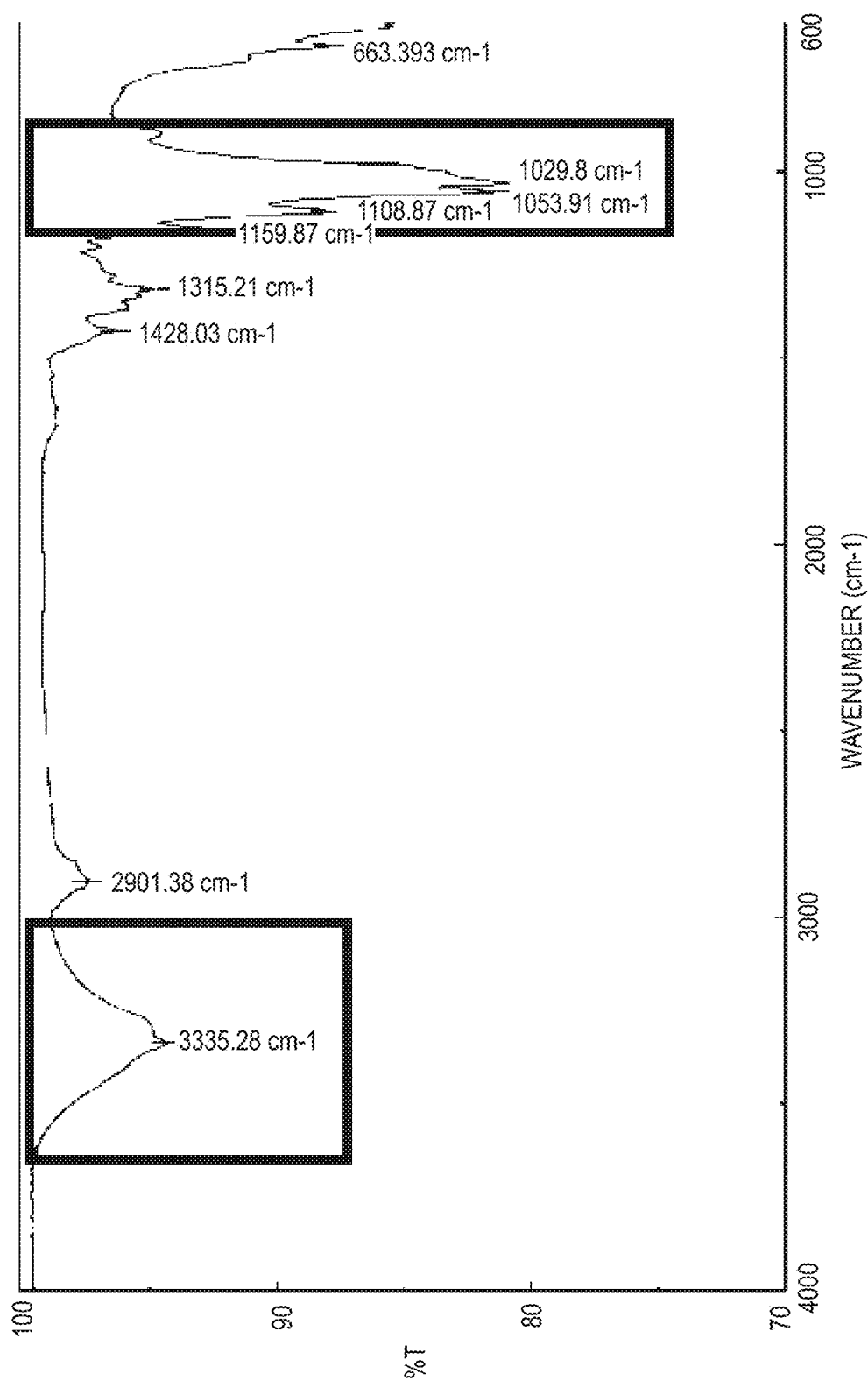
FIG. 5 is a graph illustrating the FT-IR results of cellulose recovered from cotton textile produced in accordance with some embodiments of the presently disclosed subject matter.
Figure 6:
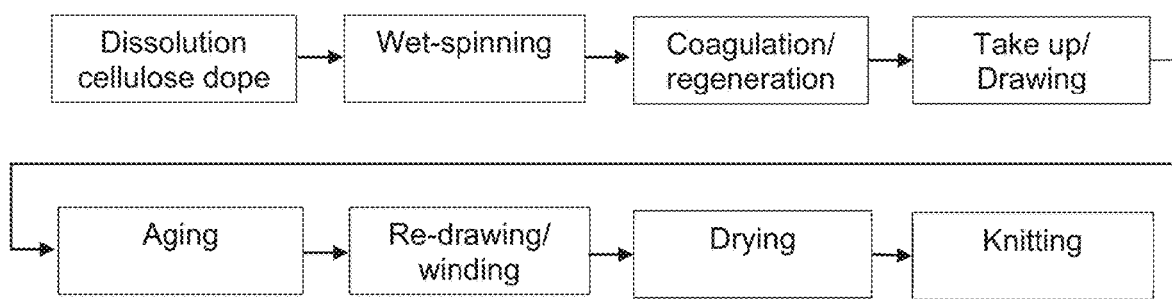
FIG. 6 is a schematic illustrating a method of producing regenerated cellulose filaments in accordance with some embodiments of the presently disclosed subject matter.
Figure 7A:
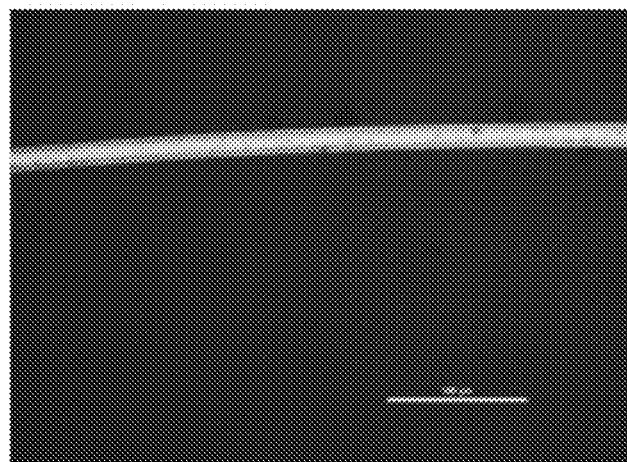
FIG. 7A is a microscopy image of a single regenerated cellulose filament produced in accordance with the presently disclosed subject matter.
Figure 7B:
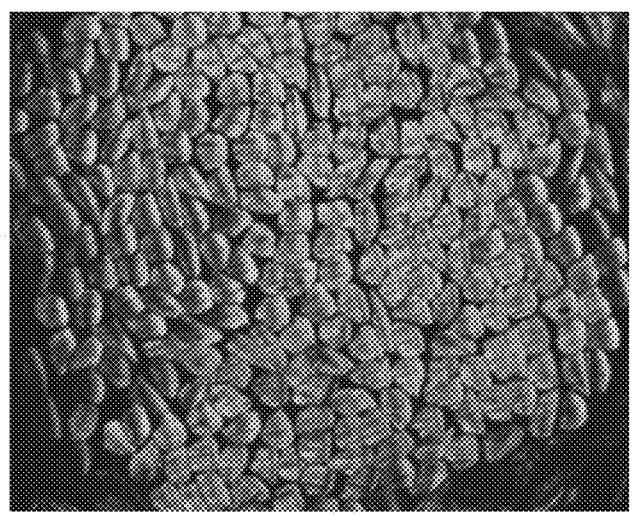
FIG. 7B is a microscopy cross-sectional image of a bundle of regenerated cellulose filament produced in accordance with the presently disclosed subject matter.
Figure 7C:
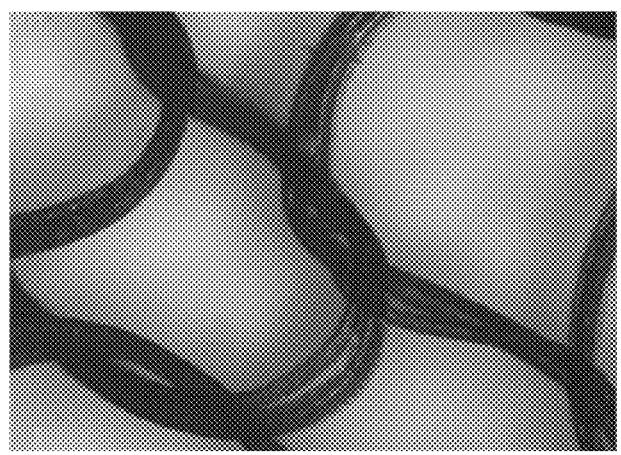
FIG. 7C is a microscopy image of a regenerated cellulose multifilament knitting sample produced in accordance with the presently disclosed subject matter.

FIG. 5 shows the results of Fourier Transform Infrared testing verifying that cellulose was recovered from the waste cotton textile treated according to the methods of the present disclosure. The purity of the recovered cellulose can range from about 94%-98% (as calculated by HPLC analysis). Cellulose dope can be used to produce continuous regenerated cellulose filament and textile products, as set forth in the schematic of FIG. 6. The cellulose monofilament produced according to the methods of the present disclosure can have a tenacity ranging from about 1.3 g/den to 1.8 g/den and a strain at break of about 10% to 12%. Optical microscopy images of regenerated cellulose filaments produced according to the methods of the present disclosure are shown in FIGS. 7a-7c. Particularly, FIG. 7a illustrates microscopy images (4×) of a regenerated cellulose filament. FIG. 7b is a cross-sectional microscopy image (4×) of a bundle filament, wherein the cross-section of each individual filament indicates an oval-alike shape. FIG. 7c is a confocal microscopy image (2×) of a knitting sample, depicting multi-filaments.

Figure 8:
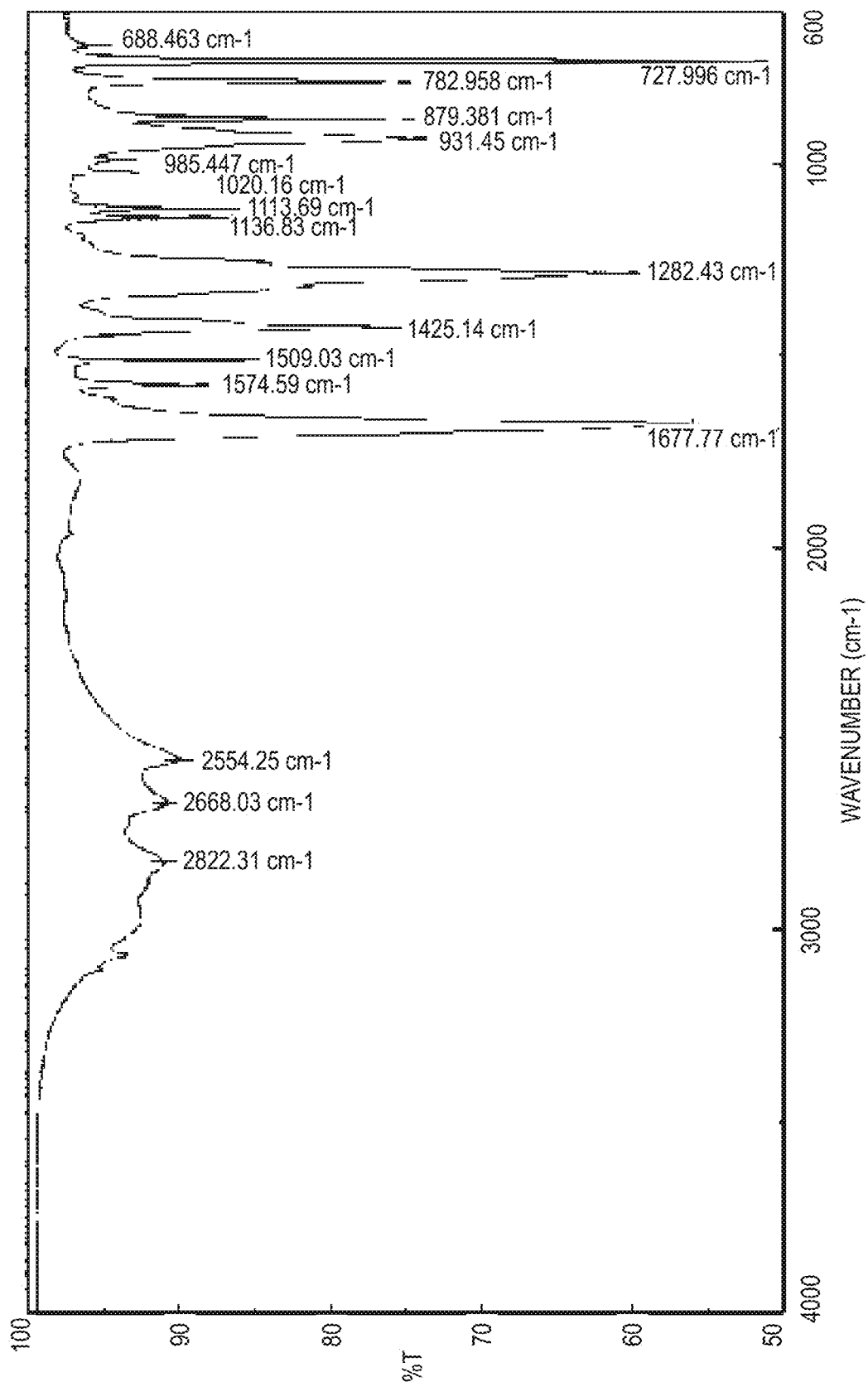
FIG. 8 is a graph illustrating FT-IR results from precipitated TPA recovered from polycotton textile produced in accordance with some embodiments of the presently disclosed subject matter.
Figure 10A:
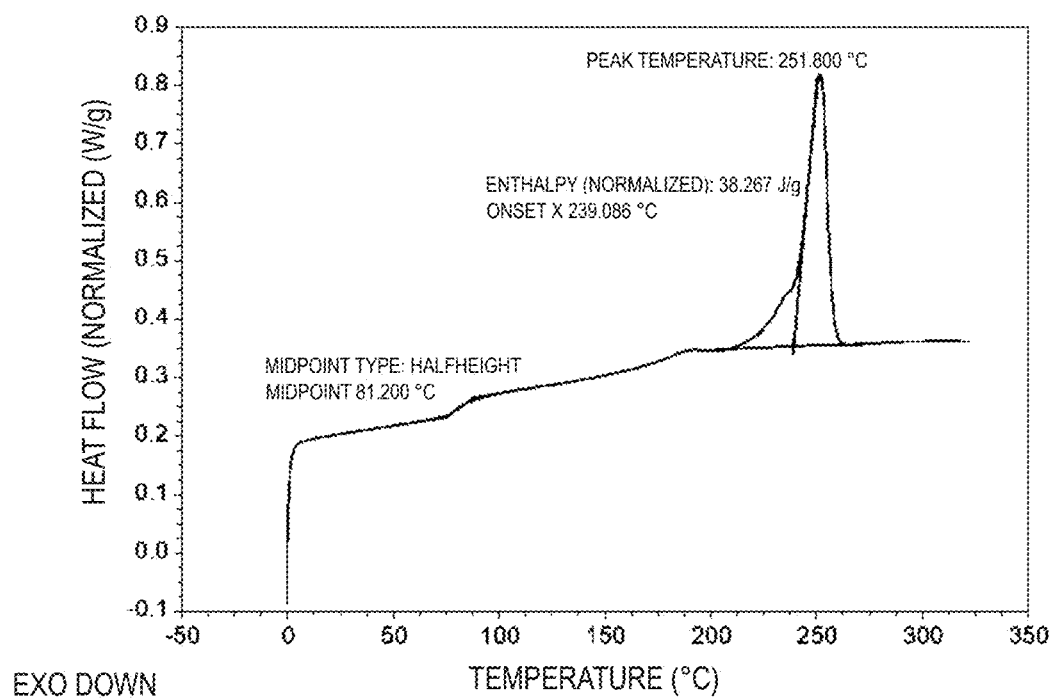
FIG. 10A is a Differential Scanning calorimetry (DSC) of regenerated PET chip produced from 100% recycled terephthalic acid (reTPA) produced in accordance with some embodiments of the presently disclosed subject matter.
Figure 10B:
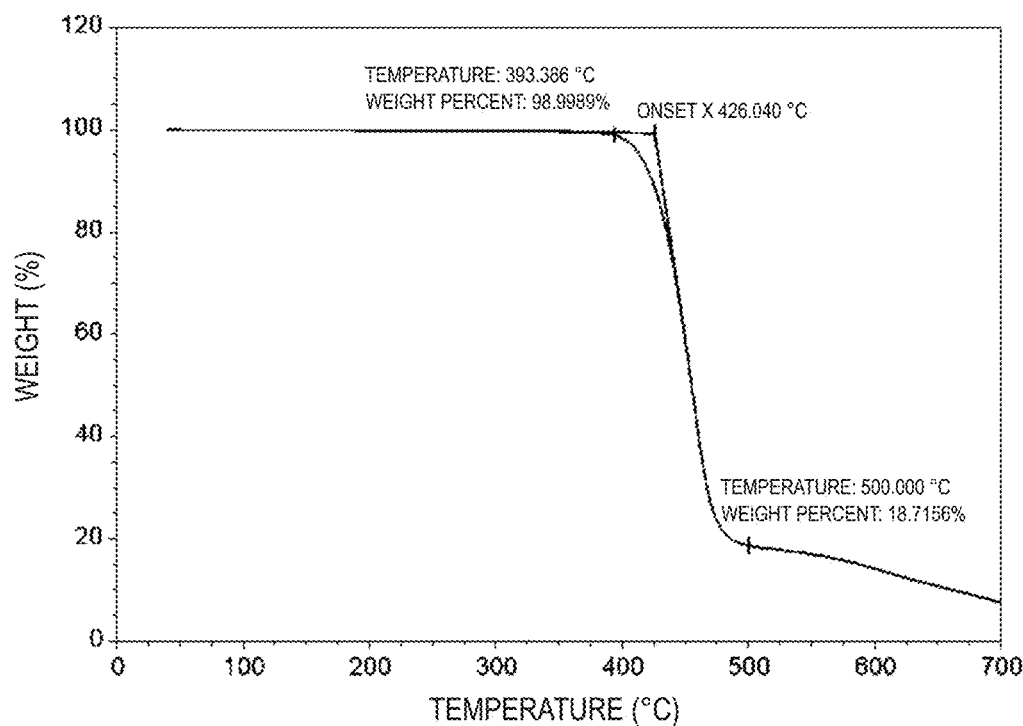
FIG. 10B is a Thermogravimetric Analysis (TGA) of regenerated PET chip produced from 100% recycled terephthalic acid (reTPA) produced in accordance with some embodiments of the presently disclosed subject matter.

EXAMPLE 11 describes the physical properties of the regenerated polyester produced from waste polycotton textiles according to the methods of the present disclosure. As described herein, polycotton textiles are subjected to subcritical water treatment such as, for example, condition II as described in Example 6, and the resulting TPA carried forward to crystallization and PET polymerization to produce regenerated PET. An FT-IR analysis of the resulting TPA is shown in FIG. 8. NMR analysis of the TPA from water recrystallization is shown in FIG. 9a. Precipitated TPA powder from the polycotton fabrics (zoomed at the aliphatic region) is shown before (FIG. 9b) and after recrystallization (FIG. 9c). FIGS. 9a-9c illustrate the reduction in impurities after recrystallization. Differential Scanning calorimetry (DSC) of regenerated PET chip produced from 100% recycled TPA according to the methods of the present disclosure is shown in FIG. 10a. As shown, The PET reference standard peak temperature is 246.139° C., and the disclosed method produced regenerated PET with a peak temperature of 251.800° C. The thermogravimetric analysis (TGA) of regenerated PET chip produced from 100% recycled TPA is shown in FIG. 10b. As shown, the PET reference standard had an onset x=425.33° C., and the disclosed method produced regenerated PET with an onset x=426.040° C.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Recycling Cotton Textiles Using Treatment with Subcritical Water for Adjusting Degree of Polymerization within the Cellulosic Pulp The method set forth in FIG. 2 can be used to recycle cotton textiles. Particularly, a sample of essentially 100% cotton waste textiles was obtained and cut into pieces, average size 5 mm. The textile pieces were introduced into a hydrothermal reactor (Parr 4553M 2-gallon reactor, available from Parr Instrument Company, Moline, Ill.) for subcritical water treatment ("Condition I"). The reactor temperature 175° C., acetic acid concentration of about 0.05%-0.1% (v/v), once the desired temperature was attained, residence time was 60 minutes, and pressure ranged from 80-120 psi. The solid:water ratio was 1:88. During the subcritical water reaction, the linkages between the fibers inside the textiles were weakened.

After subcritical water treatment, a disintegration process was performed using a standard fiber disintegrator at 2-3% cellulosic pulp concentration for 10 minutes operation time to loosen the fiber binding and to produce disintegrated cellulose. The resulting cellulosic pulp product had a viscosity of 3.2 mPa·s, which was calculated based from Equations 1, 2, 3 as about DP 240-370. The disintegrated cellulose was subjected to a separation process to recover the cellulose fiber.

Fourier Transform Infrared (FT-IR; Jasco 6200 with Pike MIRacle ATR attachment. Range: 4000-600 cm$^{-1}$, Number of scans: 128) testing was conducted to verify the presence and the type of polymer produced. As shown in FIG. 5, the results indicate cellulose was recovered from the waste cotton textile.

Example 2

Recycling Cotton Textiles Using Treatment with Subcritical Water for Adjusting Degree of Polymerization within the Cellulosic Pulp The method set forth in FIG. 2 can be used to recycle cotton textiles. Particularly, a sample of essentially 100% cotton waste textiles was obtained and cut into pieces, average size 5 mm. The textile pieces were introduced into a hydrothermal reactor (Parr 4553M 2-gallon reactor, available from Parr Instrument Company, Moline, Ill.) for subcritical water treatment ("Condition I"). The reactor temperature 155° C., acetic acid concentration of about 0.05%-0.1% (v/v), once the desired temperature was attained, residence time was 60 minutes, and pressure ranged from 80-120 psi. The solid:water ratio was 1:94. During the subcritical water reaction, the linkages between the fibers inside the textiles were weakened. The resulting cellulosic pulp product had a viscosity of 4.9 mPa·s, which was then calculated based from Equations 1, 2, 3 as about DP 450-640.

After subcritical water treatment, a disintegration process was performed using a standard fiber disintegrator at 2-3% cellulosic pulp concentration for 10 minutes operation time to loosen the fiber binding and to produce disintegrated cellulose. The disintegrated cellulose was then subjected to a separation process to recover the cellulose fiber.

Example 3

Recycling Cotton Textiles Using Treatment with Subcritical Water for Adjusting Degree of Polymerization within the Cellulosic Pulp The method set forth in FIG. 2 can be used to recycle cotton textiles. Particularly, a sample of essentially 100% cotton waste textiles was obtained and cut into pieces, average size 5 mm. The textile pieces were introduced into a hydrothermal reactor (Parr 4553M 2-gallon reactor, available from Parr Instrument Company, Moline, Ill.) for subcritical water treatment ("Condition I"). The reactor temperature 155° C., acetic acid concentration of about 0.05%-0.1% (v/v), once the desired temperature was attained, residence time was 0 minutes, and pressure ranged from 80-120 psi. The solid:water ratio was 1:31. During the subcritical water reaction, the linkages between the fibers inside the textiles were weakened. The resulting cellulosic pulp product had a viscosity of 16.8 mPa·s, which was then calculated based from Equations 1, 2, 3 as about DP 1200-1600.

After subcritical water treatment, a disintegration process was performed using a standard fiber disintegrator at 2-3% cellulosic pulp concentration for 10 minutes operation time to loosen the fiber binding and to produce disintegrated cellulose. The disintegrated cellulose was then subjected to a separation process to recover the cellulose fiber.

Example 4

Recycling Cotton Textiles Using Treatment with Subcritical Water for Adjusting Degree of Polymerization within the Cellulosic Pulp The method set forth in FIG. 2 can be used to recycle cotton textiles. Particularly, a sample of essentially 100% cotton waste textiles was obtained and cut into pieces, average size 5 mm. The textile pieces were introduced into a hydrothermal reactor (Parr 4553M 2-gallon reactor, available from Parr Instrument Company, Moline, Ill.) for subcritical water treatment ("Condition I"). The reactor temperature 155° C., acetic acid concentration of about 0.05%-0.1% (v/v), once the desired temperature was attained, residence time was 0 minutes, and pressure ranged from 80-120 psi. The solid:water ratio was 1:21. During the subcritical water reaction, the linkages between the fibers inside the textiles were weakened. The resulting cellulosic pulp product had a viscosity of 27.9 mPa·s, which was then calculated based from Equations 1, 2, 3 as about DP 1600-2000.

After subcritical water treatment, a disintegration process was performed using a standard fiber disintegrator at 2-3% cellulosic pulp concentration for 10 minutes operation time to loosen the fiber binding and to produce disintegrated cellulose. The disintegrated cellulose was then subjected to a separation process to recover the cellulose fiber.

Example 5

Recycling 100% Polyester Textiles Using Subcritical Water Treatment

The method set forth in FIG. 3 can be used to recycle polyester textiles. Particularly, a sample of essentially 100% polyester waste textiles was obtained and cut into pieces (30 cm×30 cm). The textile pieces were introduced into a hydrothermal reactor (Parr 4553M 2-gallon reactor, available from Parr Instrument Company, Moline, Ill.) for subcritical water treatment ("Condition II"). The reactor temperature was about 175° C.-180° C., with sodium hydroxide about 5% (w/v), residence time was 60 minutes, and pressure ranged from 110-140 psi. The solid/water ratio was about 1:5. After treatment, the processed solution was removed and TPA was formed by precipitation using a pH adjustment (e.g. pH 2-pH 4). The precipitated TPA was then carried forward to crystallization. This entailed heating an aqueous solution with precipitated TPA to a temperature of about 250° C. to 300° C., a ratio of solid:water of about 1:5, with a residence time of about 5 minutes. The crystalized TPA was then treated with ethylene glycol in batch autoclave at temperatures about 290° C. with Antimony metal (5b203) as catalyst for a PET polymerization process to produce regenerated PET with a target intrinsic viscosity (IV) of 0.620 dl/g.

Example 6

Recycling Polycotton Textiles Using Treatment with Subcritical Water for Adjusting Degree of Polymerization within the Cellulosic Pulp The method set forth in FIG. 4 can be used to recycle polycotton textiles.

Particularly, a sample of 80/20 polycotton (polyester:cotton=80:20) waste textiles was obtained and cut into sheets, average size 30 by 30 cm. The textile sheets were introduced into a hydrothermal reactor (Parr 4553M 2-gallon reactor, available from Parr Instrument Company, Moline, Ill.) for subcritical water treatment ("Condition II"). The reactor temperature 180° C., with sodium hydroxide about 5% (w/v), residence time was 60 minutes, and pressure ranged from 120-150 psi. The solid/water ratio was 1:11. After treatment, the dissolved TPA was recovered, and the method described above in Example 5 was used to produce regenerated PET.

In addition to the TPA, the cellulose that was produced in the subcritical water treatment was also recovered. During the subcritical water reaction, the linkages between the fibers inside the textiles were weakened, and the resulting cellulosic pulp product had a viscosity of 6 mPa·s (calculated as DP 600-800). The pulp was then washed and cut into pieces, with an average size of about 5 mm. The textile pieces were introduced into a hydrothermal reactor (Parr 4553M 2-gallon reactor, available from Parr Instrument Company, Moline, Ill.) for subcritical water treatment ("Condition I"). After subcritical water treatment, the product was washed and subjected to a disintegration process at 2-3% cellulosic pulp concentration for 10 minutes operation time to loosen the fiber binding. The disintegrated fibers were subjected to a separation process to recover the cellulose fiber. The resulting cellulosic pulp product had a viscosity of 4 mPa·s (calculated as DP 300-500).

Example 7

Recycling Polycotton Textiles Using Treatment with Subcritical Water and Phase Transfer Catalyst for Adjusting Degree of Polymerization within the Cellulosic Pulp The method set forth in FIG. 4 can be used to recycle polycotton textiles. Particularly, a sample of 80/20 polycotton (polyester:cotton=80:20) waste textiles was obtained and cut into sheets, average size 30 by 30 cm. The textile sheets were introduced into a hydrothermal reactor (Parr 4553M 2-gallon reactor, available from Parr Instrument Company, Moline, Ill.) for subcritical water treatment ("Condition II"). The reactor temperature 155° C., with sodium hydroxide about 5% (w/v), 0.5% BTBAC (w/v), residence time was 60 minutes, and pressure ranged from 120-150 psi. The solid/water ratio was 1:10. After treatment, the dissolved TPA was recovered and the method described in Example 5 was used to produce regenerated PET.

For the recovered cellulosic pulp product, during the subcritical water reaction, the linkages between the fibers inside the textiles were weakened, and the resulting product had a viscosity about 50.5 mPa·s (calculated as DP 2000-2500). The pulp was then washed and cut into pieces, with an average size of about 5 mm. The pieces were introduced into a hydrothermal reactor (Parr 4553M 2-gallon reactor, available from Parr Instrument Company, Moline, Ill.) for subcritical water treatment ("Condition I") to produce cellulosic pulp with a desired viscosity by following the methods of Example 1, 2, 3 and 4.

Example 8

Recycling Polycotton Textiles Using Treatment with Subcritical Water and Co-Solvent for Adjusting Degree of Polymerization within the Cellulosic Pulp The method set forth in FIG. 4 can be used to recycle polycotton textiles. Particularly, a sample of 80/20 polycotton (polyester:cotton=80:20) waste textiles was obtained and cut into sheets, average size 30 by 30 cm. The textile sheets were introduced into a hydrothermal reactor (Parr 4553M 2-gallon reactor, available from Parr Instrument Company, Moline, Ill.) for subcritical water treatment ("Condition II"). The reactor temperature 150° C., with sodium hydroxide about 5% (w/v), 10% MeOH (v/v), residence time was 60 minutes, and pressure ranged from 120-150 psi. The solid/water ratio was 1:10. After treatment, the dissolved TPA was recovered and the method described in Example 5 was used to produce regenerated PET.

For the recovered cellulosic pulp product, during the subcritical water reaction, the linkages between the fibers inside the textiles were weakened, and the resulting product had a viscosity about 35 mPa·s (calculated as DP 1750-2200). The pulp was then washed and cut into pieces, with an average size of about 5 mm. The pieces were introduced into a hydrothermal reactor (Parr 4553M 2-gallon reactor, available from Parr Instrument Company, Moline, Ill.) for subcritical water treatment ("Condition I") to produce cellulosic pulp with a desired viscosity by following the methods of Example 1, 2, 3 and 4.

Example 9

Recovery of Cotton Fibers from Polycotton Textiles

Polycotton textiles were subjected to the subcritical water treatment (condition II) described in Example 8. After the treatment, the TPA was dissolved, and the cellulose materials were recovered with a viscosity about 35 mPa·s (calculated as DP 1750-2200). The cotton sheets were then shredded and disintegrated for use as staple fibers to blend with virgin cotton fibers or other fibers as recycled cotton blend yarn.

Example 10

Regenerated Cellulose Filament Produced from Recycling Polycotton Textiles

The cellulosic pulp product that resulted from the method of Example 6 was subjected to a sour wash process with diluted aqueous sulfur dioxide solution (pH 2-pH 3), 1:20 (cellulose sample:aqueous solution) and stirred for 1.5 hours at room temperature. The sour washed pulp was then filtered, washed with DI water until neutral pH was obtained, and air dried. A cellulose fiber activation process was performed that included producing a ground cellulose pulp sample in aqueous NaOH solution (15% w/v), 1:20 (cellulose sample:aqueous solution), stirring for 4 hrs at room temperature, then washing to neutral pH, drying, treating with 1M sulfuric acid at room temperature for about 45 mins, then washing to neutral pH, and air drying.

To make the cellulose dissolution dope, the activated cellulose sample was incorporated into Lithium Chloride (8% w/v)/N, N-dimethylacetamide with Lauryl gallate (10% w/w versus added cellulose sample) and mucic acid (5% w/w versus added cellulose sample) as the additives, stirring at 120° C. to 130° C. for about 90 mins, cooling down, then centrifugation at 2500 rpm for about 60 mins to remove the undissolved impurities and to make the dissolution cellulose dope in a solid concentration about 4% to 6%. Then the cellulose dope was used to produce continuous regenerated cellulose filament and textile products, as set forth in the schematic of FIG. 6.

The physical properties of the regenerated cellulose monofilament were measured. The monofilament had a tenacity ranging from 1.3 g/den to 1.8 g/den and a strain at break of about 10% to 12%.

Optical microscopy images were taken of the produced regenerated cellulose filaments. Particularly, FIG. 7a illustrates microscopy images (4×) of a single regenerated cellulose filament. FIG. 7b is a cross-sectional microscopy image (4×) of a bundle filament, wherein the cross-section of each individual filament indicates an oval-alike shape. FIG. 7c is a confocal microscopy image (2×) of a knitting sample, depicting multi-filaments.

Example 11

The Physical Properties of Regenerated Polyester Produced from Recycling Polycotton Textiles Polycotton textiles were subjected to the subcritical water treatment (condition II) described in Example 6, and then the dissolved TPA was recovered by precipitation using a pH adjustment (e.g. pH 2-pH 4). The precipitated TPA was then carried forward to crystallization. This entailed heating an aqueous solution with precipitated TPA to a temperature of about 250° C. to 300° C., a ratio of solid:water of about 1:5, with a residence time of about 5 minutes. The crystalized TPA was then treated with ethylene glycol in batch autoclave at temperatures about 290° C. with Antimony metal ($Sb_2O_3$) as catalyst for a PET polymerization process to produce regenerated PET with a target intrinsic viscosity (IV) of 0.620 dl/g.

FT-IR (Jasco 6200 with Pike MIRacle ATR attachment. Range: 4000-600 $cm^{-1}$, Number of scans: 128) testing was conducted to analyze the TPA produced during the TPA precipitation step, as shown in FIG. 8.

NMR analysis of the crystallized TPA from water recrystallization is shown in FIG. 9a. Precipitated TPA powder from the polycotton fabrics (zoomed at the aliphatic region) is shown before (FIG. 9b) and after recrystallization (FIG. 9c). As shown, after recrystallization, a reduction in impurities was observed.

The Differential Scanning calorimetry (DSC) of regenerated PET chip produced from 100% recycled TPA is shown in FIG. 10a. DSC analysis was performed using a TA Instruments Discovery Model DSC utilizing a "heat-cool-heat" method to remove any thermal history based on processing history. The second heating scan was performed from (either 0 or −90° C.) to 325° C. at a rate of 10° C. As shown, The PET reference standard peak temperature is 246.139° C., and the disclosed method produced regenerated PET with a peak temperature is 251.800° C.

The thermogravimetric analysis (TGA) of regenerated PET chip produced from 100% recycled TPA is shown in FIG. 10b. TGA analysis was performed using a TA instruments Discovery Model TGA utilizing a temperature ramp from room temperature to 700° C. at a rate of 20° C./min under nitrogen atmosphere. As shown, the PET reference standard onset x=425.33° C., and the disclosed method produced regenerated PET with an onset x=426.040° C.

What is claimed is:

1. A method of producing terephthalic acid (TPA) from a polyester waste textile material, the method comprising:
    treating the polyester waste textile material in a subcritical water reactor at a temperature of about 105° C. to 190° C., a pressure of about 40 to 300 psi, or both for about 0 to 90 minutes, wherein a dissolved TPA and ethylene glycol (EG) is produced, and wherein a regenerated polyethylene terephthalate (PET) produced from the TPA has a peak temperature as measured by differential scanning calorimetry and an onset temperature as measured by thermogravimetric analysis within +/−5% of that of standard reference PET.

2. The method of claim 1, wherein the regenerated PET produced from the TPA has the onset temperature as measured by thermogravimetric analysis within +/−1% of that of standard reference PET.

3. The method of claim 1, wherein the regenerated PET produced from the TPA has the peak temperature as measured by differential scanning calorimetry within 2.3% of standard reference PET or the onset temperature as measured by thermogravimetric analysis within 0.2% of that of standard reference PET.

4. The method of claim 1, wherein the treating in the subcritical water reactor comprises a pH ranging from about 10-14.

5. The method of claim 1, wherein the treating in the subcritical water reactor comprises about 5% (w/v) sodium hydroxide.

6. The method of claim 1, wherein the polyester waste textile material/water ratio is about 1:5.

7. The method of claim 1, further comprising recovering the TPA.

8. The method of claim 7, wherein the recovering the TPA is carried out using a pH adjustment of about pH 2-pH 4.

9. The method of claim 8, further comprising treating the recovered TPA with ethylene glycol in a PET polymerization process to produce the regenerated PET.

10. The method of claim 9, wherein the treating comprises an autoclave at temperatures about 290° C. with Antimony metal ($Sb_2O_3$) as catalyst.

11. The method of claim 9, wherein the regenerated PET has an intrinsic viscosity of about 0.620 dl/g.

12. The method of claim 1, further comprising recovering the ethylene glycol.

13. The method of claim 12, wherein recovering the ethylene glycol comprises vacuum distillation.

14. The method of claim 1, further comprising recovering the TPA and recovering the ethylene glycol.

* * * * *